United States Patent
Kazemzadeh

(10) Patent No.: US 7,270,648 B2
(45) Date of Patent: Sep. 18, 2007

(54) DRUG DELIVERY APPARATUS

(76) Inventor: Farhad Kazemzadeh, 8221 Amsden Rd., Bloomington, MN (US) 55428

( * ) Notice: Subject to any disclaimer, the term of this patent is extended or adjusted under 35 U.S.C. 154(b) by 642 days.

(21) Appl. No.: 10/328,491

(22) Filed: Dec. 23, 2002

(65) Prior Publication Data

US 2004/0122366 A1    Jun. 24, 2004

(51) Int. Cl.
*A61M 5/20*    (2006.01)
(52) U.S. Cl. .................................................. 604/135
(58) Field of Classification Search ............ 604/131, 604/134, 135, 181, 183, 187, 191, 246; 128/DIG. 1, 128/DIG. 12
See application file for complete search history.

(56) References Cited

U.S. PATENT DOCUMENTS

| | | | |
|---|---|---|---|
| 2,295,489 A | | 9/1942 | Kayden |
| 3,685,697 A | * | 8/1972 | Caslow et al. ............... 222/137 |
| 4,180,067 A | | 12/1979 | Derlien |
| 4,857,056 A | * | 8/1989 | Talonn ......................... 604/135 |
| 4,863,429 A | * | 9/1989 | Baldwin ...................... 604/135 |
| 4,921,487 A | | 5/1990 | Buffet et al. |
| 6,605,066 B1 | * | 8/2003 | Gravagna et al. ............ 604/191 |
| 2001/0021830 A1 | | 9/2001 | Yamada et al. |
| 2001/0056259 A1 | | 12/2001 | Shinkle et al. |
| 2004/0034276 A1 | * | 2/2004 | Voellmicke et al. ........... 600/36 |

FOREIGN PATENT DOCUMENTS

| | | |
|---|---|---|
| EP | 0344 895 | 6/1989 |
| WO | WO88/10129 | 12/1988 |
| WO | WO 97/28835 | 8/1997 |
| WO | WO97/28835 | * 8/1997 |
| WO | WO 01/97901 | 12/2001 |

* cited by examiner

*Primary Examiner*—Matthew F. DeSanto
(74) *Attorney, Agent, or Firm*—Thomas J. Nikolai; Nikolai & Mersereau, P.A.

(57) ABSTRACT

A drug to be infused into a patient is contained in a syringe or vial having a displaceable plunger for ejecting the drug out through an injection port into an administration set. Motion of the plunger of the drug delivery syringe/vial is controlled by a driver syringe having a piston or plunger for ejecting either a compressible or an incompressible fluid through a flow resistance element. Motive power for the piston of the drive syringe is provided by a constant load spring. A suitable linkage is provided for coupling the piston of the drive syringe to the plunger of the drug delivery syringe. Several types of flow rate control elements for use with the driver syringe are disclosed.

8 Claims, 16 Drawing Sheets

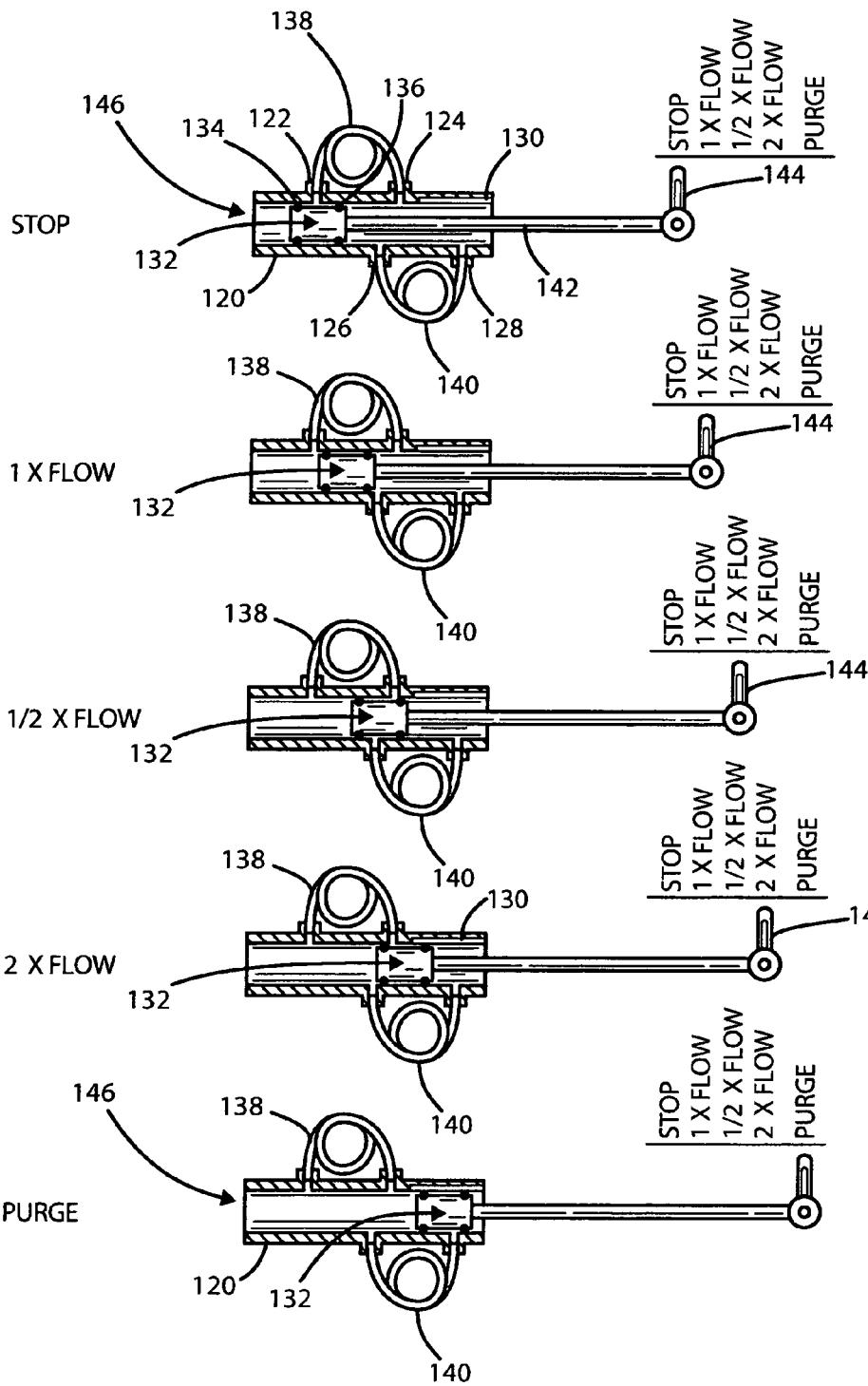

2 X FLOW

1/2 X FLOW

1 X FLOW

STOP

DRUG DELIVERY APPARATUS

BACKGROUND OF THE INVENTION

I. Field of the Invention

This invention relates generally to a dispenser for the controlled delivery of parenteral medication or interal solution into a patient and more particularly to a purely mechanical drug injection system for precisely controlling the flow rate of the medication from a syringe or vial into a patient.

II. Discussion of the Prior Art

Drug infusion has been around since the event of a long-term vascular access shunt which facilitates the continuous administration of intravenous antibiotics and nutritional solutions. To improve patient mobility and to increase the accuracy of the delivery rate, other means of drug infusion, such as electronic pumps and low-cost mechanical pumps have been devised. Electronic pumps, such as motorized syringe pumps, are accurate, but require a power source, such as batteries or a power line for its operation and they tend to be bulky and pole mounted. Comparable mechanical pumps are less accurate and tend to afford fewer features than are provided by electronic pumps. They do, however, offer an advantage of lower cost, greater portability and single-use disposability. Other known types of disposable infusion pumps, such as elastomeric pumps, have been developed for fixed flow rate applications.

Presently, with strong control by insurance companies on the treatment cost of diseases involving infusion, a low-cost reliable and disposable device, exhibiting a lower chance of infection, in comparison to other multiple use delivery devices are advantageous. Infusion therapies, such as pain management, chemotherapy and diabetes care, require higher infusion accuracy as well as stricter drug stability and biocompatibility requirements in comparison to antibiotic therapy.

The bio/drug compatibility problem becomes more of an issue for long-term, slow, infusion and applications requiring low volume of drug, such as insulin, where the ratio of drug contacting surface to drug volume is high. Similarly, therapies requiring drugs at low concentration, drugs with very short half-life, drugs soluble in lipid or high polar solutions provide insurmountable challenges for selection of material that contacts the drug. Similarly, applications such as inter-muscular drug infusion applications, require the highest level of bio-compatibility and the lowest level of leachability for drug contact material. Bio-compatibility tests are expensive and tend to be quite time consuming and must be performed on all material contacting the drugs in the delivery device. Syringe pumps, using approved syringes and administration sets require minimal bio-compatibility and drug stability and leachability testing. Syringe pumps which interfere with drug flow for the purpose of controlling the flow, such as spring-powered syringe pumps with capillary rate control, require material bio-compatibility and drug stability and solution leachability testing for materials used in the rate control element, connectors and non-standard administration line.

Elastomeric pumps with high elastomeric surface contact, as well as numerous parts that contact the drug must undergo additional material tests. The material used in drug contacting flow control elements must also pass compatibility testing. The delivery platforms where the drug is metered by a flow control element, such as spring-loaded syringe pumps, and almost all elastomeric-powered pumps, further suffer from dependence of delivery accuracy on physical properties of the drug. The drug solution's physical properties, such as viscosity or density, can cause delivery rate changes due to changes in drug concentration or changes in the use environment, such as temperature changes. Prior art mechanical disposable syringe pumps provide a constant delivery rate by either providing a constant velocity motion to the plunger of a syringe by some clock-type mechanism, such as is described in U.S. Pat. No. 4,602,700 or by pressurizing the drug in the syringe and placing a flow resistance element in the delivery flow circuit. Here, reference is made to U.S. Pat. Nos. 4,289,006, 4,381,006 and 4,755,172. Such clock-type mechanisms tend to be complex, typically have many moving parts and are not capable of providing a driving force to overcome frictional resistance encountered in larger syringes. A disposable syringe driver that controls the flow rate of pressurized drugs requires a flow restriction element in the drug delivery circuit. Such an arrangement exhibits the further disadvantages of mandating a non-standard administration line in order to adapt to the configuration of the flow resistance element. Moreover, dependence of the delivery rate on the type of drug and its concentration. Further, such prior art devices exhibit a variation in drug delivery rate with environmental changes, such as temperature, which may impact the viscosity of the drug and, therefore, its flow rate. For these reasons, a need exists for an improved drug delivery apparatus that obviates most, if not all, of the foregoing problems is needed. It is the primary object of the present invention to provide just such a device.

SUMMARY OF THE INVENTION

In accordance with the present invention, there is provided a fluid dispensing device that comprises a first syringe having a reservoir with an outlet port, where the reservoir is adapted to hold a fluid medicament to be dispensed along with a plunger for ejecting the fluid from the reservoir through the outlet port. A second syringe is also provided that has a reservoir with an outlet port where the reservoir of the second syringe is adapted to contain a fluid and a plunger for ejecting the fluid from the second reservoir. A flow rate control device is coupled to the outlet port of the reservoir of the second syringe and a mechanical linkage is used to couple the plunger of the second syringe to the plunger of first syringe. A suitable, constant-force spring is operatively coupled to the plunger of the second syringe to impart a compressive force to the plunger of the second syringe to eject the fluid contents through the rate control device. As the plunger of the second syringe moves under pressure from the constant force spring, the link member is simultaneously depressing the plunger of the first syringe to eject the medicament from the reservoir of the first syringe directly into the patient or into an administration set that is coupled to the outlet port of the first syringe.

The second syringe along with the constant force spring acting upon its plunger thus comprises a syringe driver mechanism for the syringe containing the medicament. In accordance with a further feature of the invention, the mechanical syringe driver can impart a step-wise motion or a continuous motion to the plunger of the first syringe.

DESCRIPTION OF THE DRAWINGS

The foregoing features, objects and advantages of the invention will become more apparent to those skilled in the art from the following detailed description of a preferred embodiment, especially when considered in conjunction with the accompanying drawings in which like numerals in the several views refer to corresponding parts:

FIGS. 9a through 9e illustrate a first embodiment of a multi-mode rate control device adapted to be coupled to an outlet port of the syringe driver's reservoir;

DESCRIPTION OF THE PREFERRED EMBODIMENT

Figure 1:
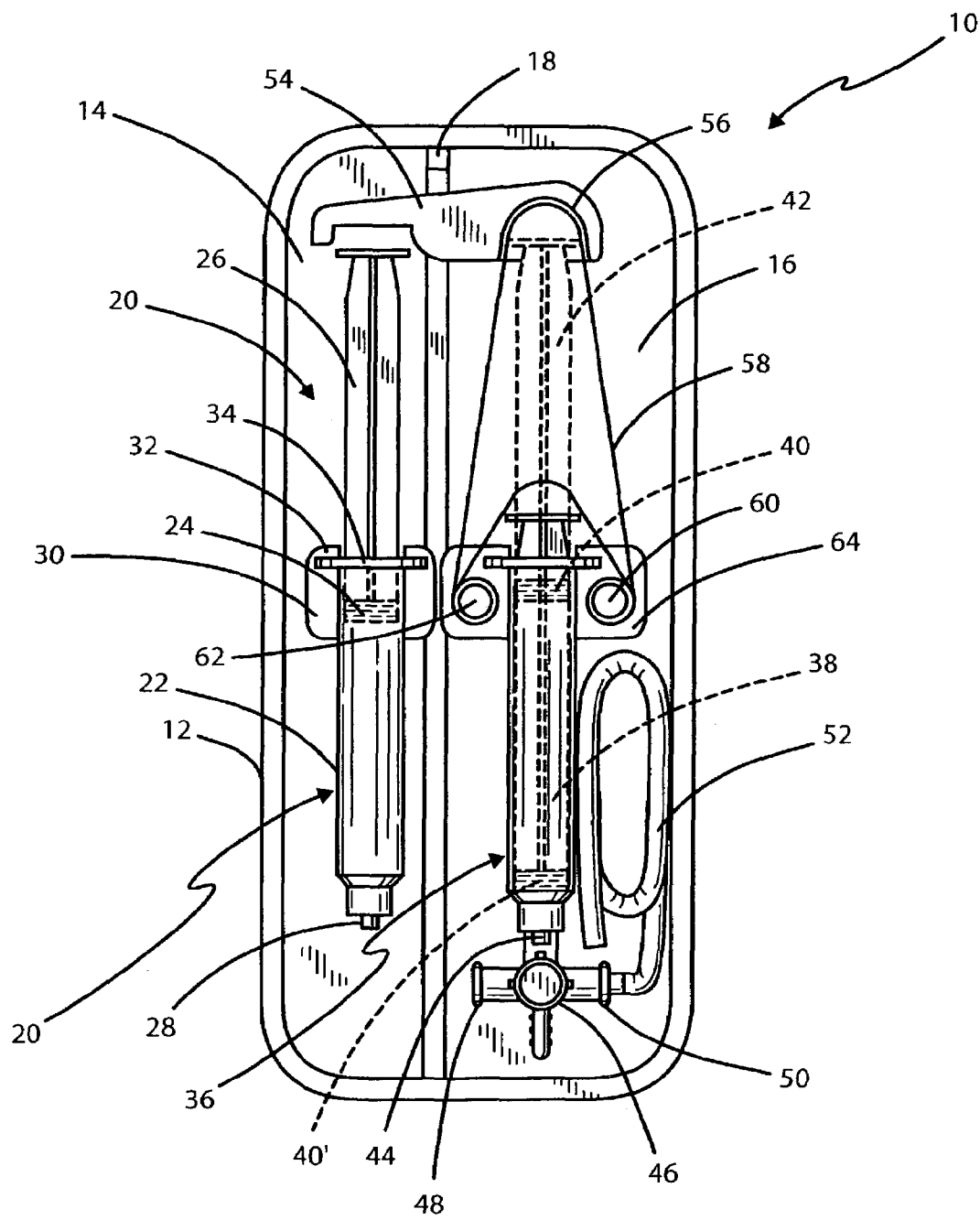
FIG. 1 is a front elevation view of a first embodiment of the present invention.

Referring first to FIG. 1, there is indicated generally by numeral 10 a fully mechanical dispenser for the controlled delivery of a liquid medicament to a patient. The device 10 is seen to comprise a molded plastic or metal housing 12 that is effectively divided into two compartments 14 and 16 by a longitudinally extending rail 18 that is integrally molded with the housing 12. Contained within the compartment 14 is a first syringe 20 of a conventional design having a glass or plastic reservoir 22 containing the drug to be administered. Fitted into the reservoir is an elastomeric plunger 24 that is affixed to a lower end of a plunger rod 26. The reservoir 22 has an outlet port 28 at a distal end thereof and which is adapted to be coupled to an ejection site on an administration set (not shown) leading to the patient. Depression of the plunger 26, of course, forces the liquid medicament from the reservoir 22 out through the outlet port 28 of the syringe 20. As used throughout the specification and claims hereof, when reference is made to a "syringe" used to contain and eject a medicament, it is meant to include a drug delivery vial, as well.

The housing 12 further includes stationary brackets 30 having slots 32 formed therein for capturing and retaining a flange 34 disposed at the upper end of the reservoir 22 when the syringe is dropped into the housing compartment 14. The engagement of the bracket with the flange precludes movement of the reservoir portion of the syringe 20 within the housing as its plunger 26 is depressed.

Located within the compartment 16 of the housing 12 is a syringe driver which itself comprises a second syringe 36. The syringe 36 includes a reservoir 38 for containing either a compressible or an incompressible fluid, along with an elastomeric piston or plunger 40 disposed on the lower end of a plunger rod 42. The reservoir 38 of the syringe driver 36 has an outlet port 44 and shown fitted over the outlet port 44 is a conventional stop cock 46. A first outlet 48 of the stop cock 46 is shown as being opened to the atmosphere while a second port 50 is coupled to the inlet end of a flow regulator 52 which, as shown in FIG. 1, may comprise a capillary tube whose lumen diameter and overall length provides a fixed, predetermined flow resistance which may be adjusted to the pressure and viscosity of the fluid contained within the reservoir 38 to provide a desired speed of movement to the plunger 42.

The plunger 42 is coupled by a linkage 54 to the plunger 26 of the syringe 20, and it is adapted to be guided in its travel by the rail 18. The linkage 54 is clamped to the plunger 42 and moves with it. A rounded arcuate slot 56 is preferably formed in the linkage 54 for receiving a portion of a constant force spring 58 therein when inserted from the front. The coiled end portions 60 and 62 of the constant force spring are disposed about posts projecting outwardly from the bracket 64 that is used to hold the reservoir 38 against longitudinal displacement as the plunger 40 descends due to the force of the spring 58. In FIG. 1, the plunger 42 is shown in dotted line representation in its elevated disposition and in solid line form in its fully inserted disposition identified by numeral 40'.

If it is desired to rapidly purge the fluid in the drive syringe reservoir 38, the stop cock 48 is turned such that the outlet port 44 of the reservoir is in fluid communication with the ambient via stop cock 48. Here, there is very little resistance to the outflow of the fluid from the reservoir 38. It also follows that the plunger 24 of the first syringe 20 descends rapidly to eject the medicament from the reservoir 22. When the stop cock is turned so as to place the outlet port 44 of the drive syringe in fluid communication with the flow regulator 52, the speed at which the plunger 40 moves within the barrel 38 is determined by the flow resistance afforded by the flow regulator 52.

From what has been thus far described, those skilled in the art will appreciate that the motion of the driver syringe is coupled to the motion of the medication-containing syringe. Therefore, the medication is delivered in a flow pattern dictated by the motion of the plunger of the driver syringe. The rate at which the plunger in the driver syringe moves is tailored by a flow restrictor coupled to the outlet port of the driver syringe. Hence, the speed at which the plunger of the drug containing syringe moves is independent of the physical characteristics of the drug being delivered.

Figure 2A:
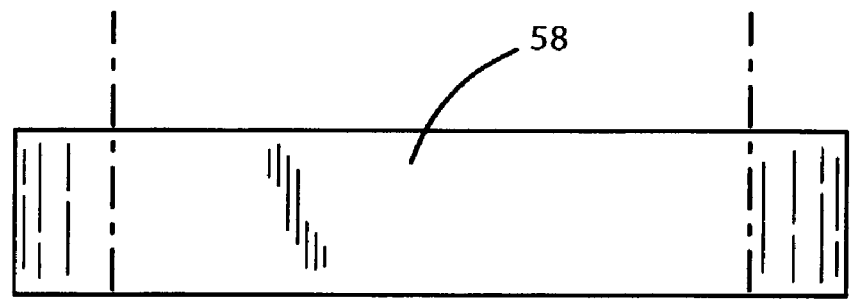
FIGS. 2a and 2b are, respectively, a top view of a constant force spring and a side view of that spring that is used in the drug delivery device of FIG. 1.
Figure 2B:
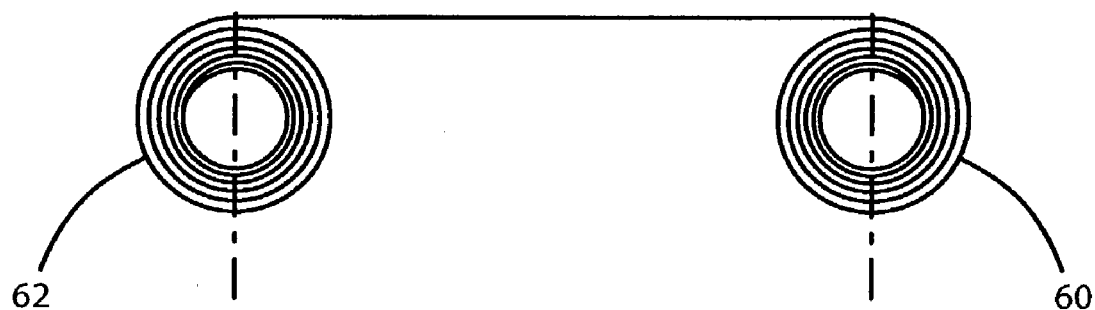

Referring next to FIGS. 2a and 2b, there is illustrated a top view and a side view of the constant force spring 58. It is seen to comprise a strip of stainless steel metal bent to form a spiral shape at opposed ends 60 and 62. When the spring is deflected by pulling out the midsection, a resisting force results that has a line of action through the plunger. This force does not increase with increasing deflection (extension) as in a conventional extension spring. The change from the original curvature of the material to a somewhat straightened condition as it passes around the slot 56, energy is stored in the straightened sections. The force directed onto the plunger of the drive syringe results from the tendency of the spring material to recoil around the posts. This force exerted by the spring remains substantially constant over the entire length of travel of the plunger 40.

Figure 3:
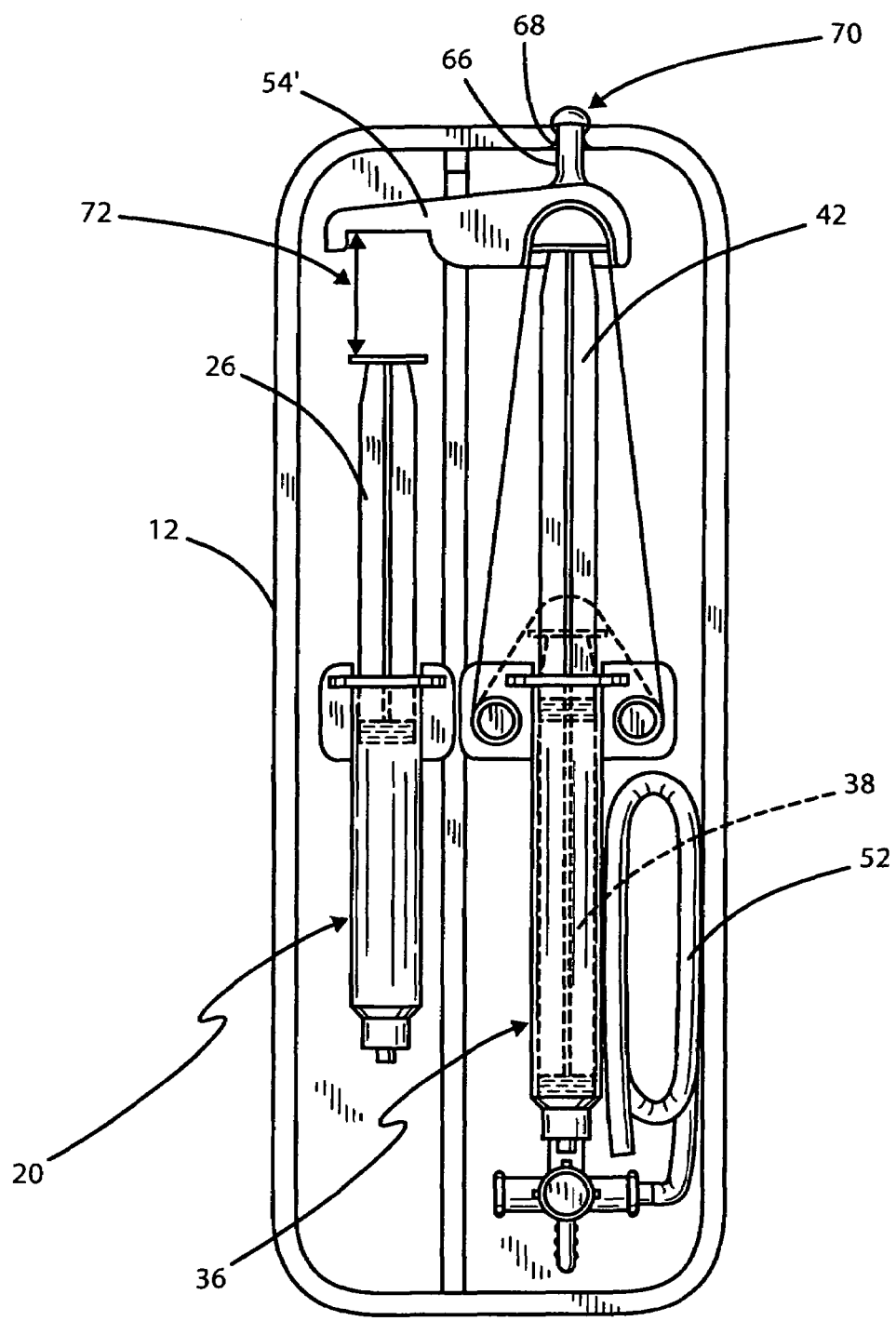
FIG. 3 illustrates by means of a front view, the initial position of the syringe driver relative to the drug delivery syringe when the syringe reservoir of the driver contains a compressible fluid.

FIG. 3 is a front view of the drug delivery apparatus of the present invention when a compressible fluid, e.g., air, is contained in the reservoir 38 of the drive syringe 36. Here, the pusher linkage 54' includes an upwardly projecting stem 66 that passes through an aperture 68 formed in the housing 12. The stem terminates in a resilient pushbutton member 70. The pusher link 54' is shown in the position it would be at the start of an ejection cycle and it is to be noted that a predetermined gap, represented by double-headed arrow 72, is present between the pusher linkage and the top of the plunger 26 of the drug syringe 20. This initial space is calculated depending upon the design pressure of the driver syringe 36. Higher pressure in the driver syringe requires a larger initial gap. By pressing the resilient button 70 through the aperture 68, the discharge cycle is begun. The plunger 42 begins its descent and when the point is reached at which the pusher linkage 54' comes into contact with the head of the plunger 26, it too begins to descend at a rate determined by the flow regulator 52.

Figure 4:
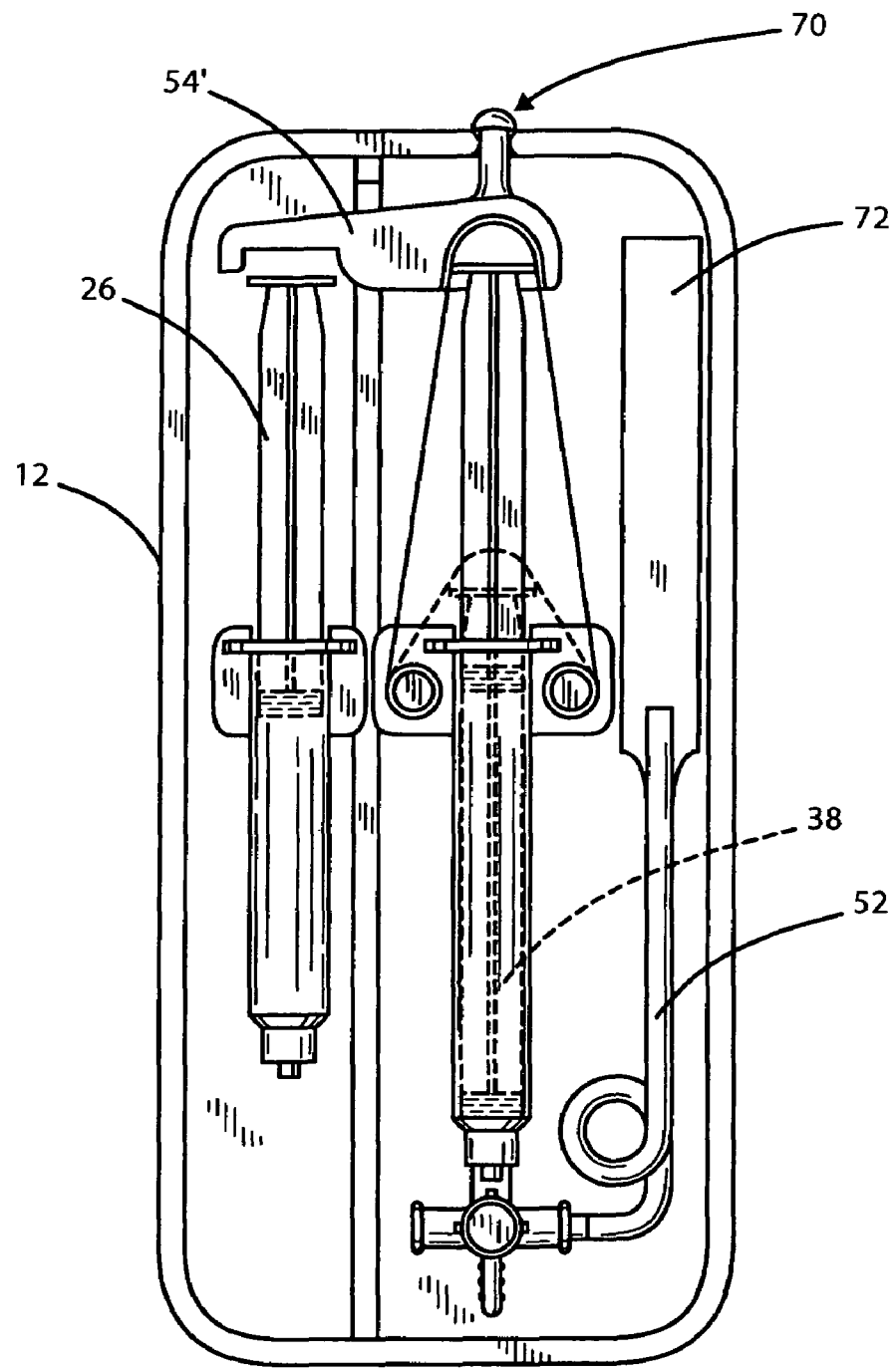
FIG. 4 is a front view illustrating the addition of a collection chamber for an incompressible fluid being ejected from the driving syringe.

FIG. 4 is included to illustrate the configuration of FIG. 1 when an incompressible fluid is contained within the driver syringe 38. Here, the gap between the start position of the pusher linkage 54' and the upper end of the plunger 26 is only made sufficiently large to permit the first syringe 20 to be inserted into the holding bracket of the housing 12 without contacting the pusher linkage 54'.

With continued reference to FIG. 4, it also illustrates the addition of a flexible bag 72 that is sealed to the end of the flow regulator capillary 52 for safe storage of the incompressible fluid contained within the reservoir 38 of the driver syringe 36.

Figure 5:
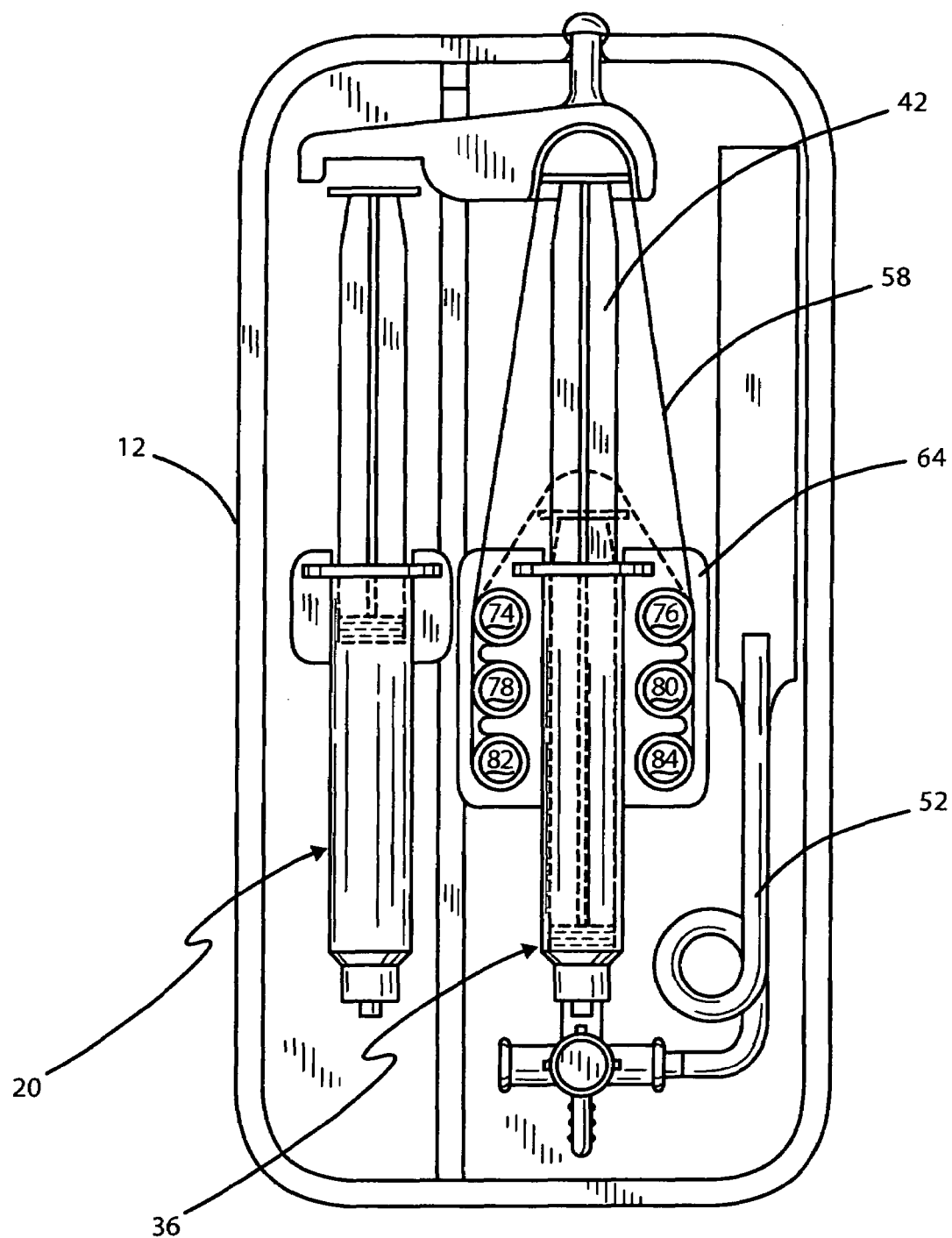
FIG. 5 is a front elevation view of a preferred embodiment incorporating a multi-coil constant force spring.

Turning next to FIG. 5, it differs from the basic configuration illustrated in FIG. 1 in that instead of the constant force spring 58 having only two helical segments mounted to the stationary bracket 64, in the embodiment of FIG. 5, multiple coils 74-76, 78-80, and 82-84 are provided thereon. This multi-coil spring set up may be used to increase the driving force on the plunger 42. Those skilled in the art will appreciate that the spring force can be increased by other means, e.g., by increasing the width or thickness or the modulus of the spring material. The multi-cord spring arrangement illustrated in FIG. 5 also accommodates slight load increases by addition of very light springs to improve the load tolerance. The friction between the springs is negligible due to lack of sliding motion between the convolutions of the helical springs. It is also contemplated that the width of the spring may be varied along its length dimension to provide force patterns of increasing, decreasing or step function variations in applied force to suit specific desired delivery requirements.

Figure 6:
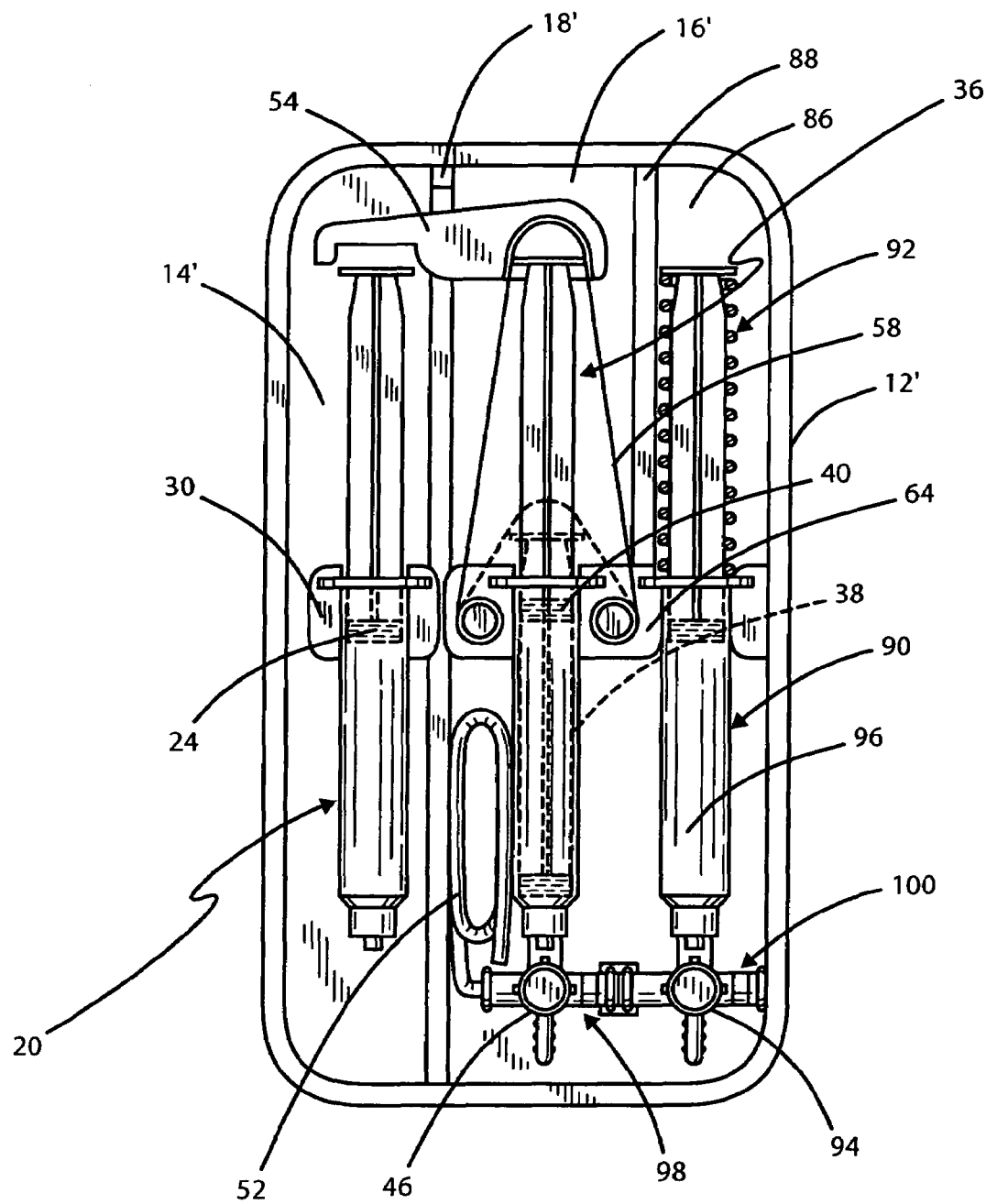
FIG. 6 is a front elevation view of the preferred embodiment along with an auxiliary pump for pressurizing the reservoir of the driver syringe with a compressible fluid.

Next, with reference to FIG. 6, the housing 12' is effectively divided into three compartments 14', 16' and 86 by rails 18' and 88. Integrally formed through the housing are holding brackets 30 and 64 for retaining a drug delivery syringe 20 and a driver syringe 36. Again, a pusher linkage 54 is affixed to the movable plunger of the drive syringe 36. A constant force spring 58 is arranged to apply a force on the plunger 40 to displace a fluid contained within the reservoir 38 through the stop cock 46 and through a flow resistor element 52. The flow resistor is again shown here as a capillary tube of a length and internal diameter providing a desired resistance to the flow of fluid from the drive syringe 36. Syringe 36 ultimately controls the speed of descent of the plunger 24 and the rate at which the medicament is ejected from the syringe 20.

Contained within the compartment 86 is a further syringe that is used as a pump to initially pressurize the driver syringe 36 for single or multiple use applications. More particularly, the syringe 90 has a spring-loaded plunger rod 92 which is adapted to be reciprocally depressed by a user. With the stop cocks 46 and 94 being appropriately positioned, during a down stroke of the plunger rod 92, air contained in the reservoir 96 of the syringe 90 is forced through the one-way valve 98 and into the reservoir 38 of the driver syringe 36. When finger pressure is released on the plunger rod 92, the spring raises the plunger drawing air into the reservoir 96, via the one-way valve 100. Repeated actuation of the syringe pump 90 increases the pressure within the reservoir the drive syringe, the greater pressure within the reservoir 38, the longer it will take for the constant force spring 58 to effect the descent of the pressure linkage 54 and the resulting delivery of the drug from the syringe 20 which can be manipulated as a delivery delay mechanism.

Figure 7:
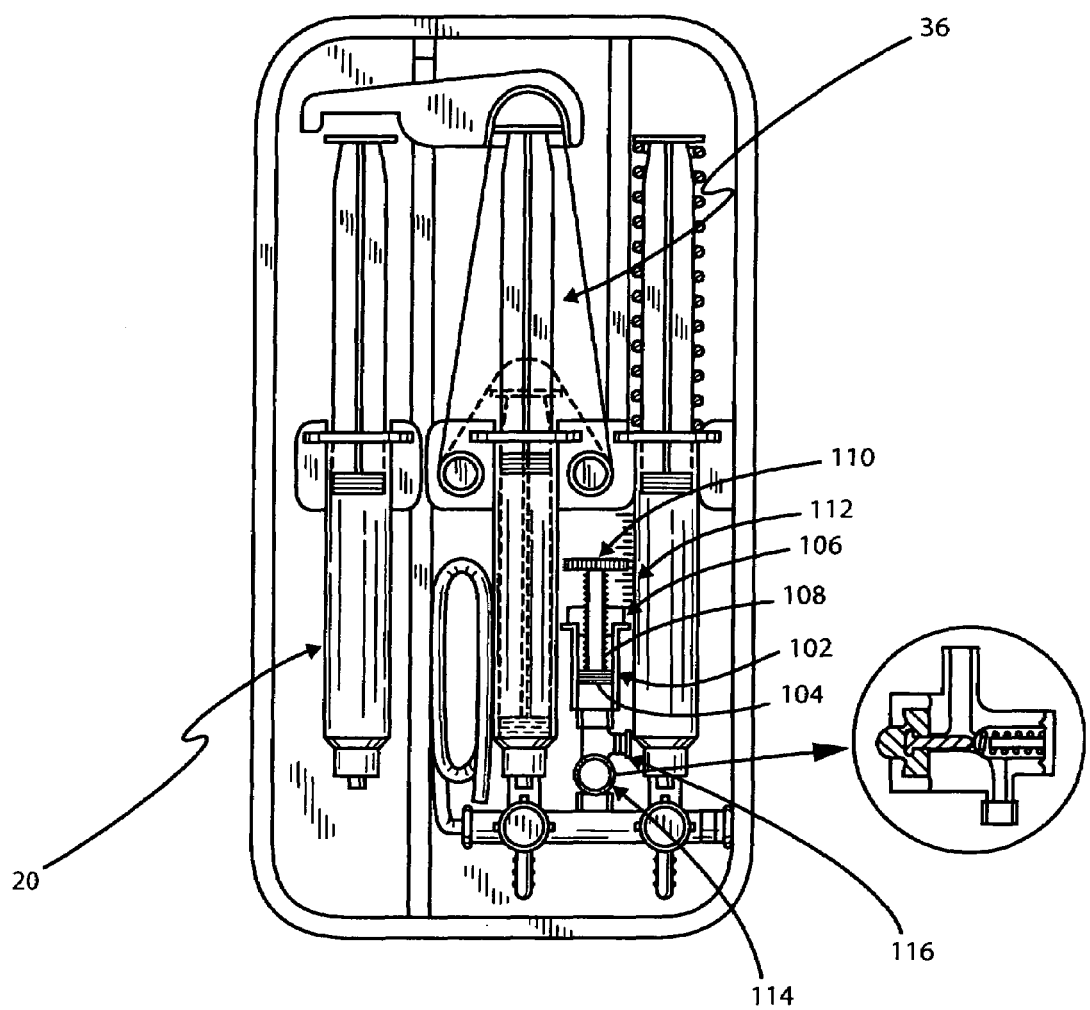
FIG. 7 is a front elevation view of an alternative embodiment providing for the administration of a bolus dose.

FIG. 7 illustrates a modification to the preferred embodiment whereby bolus volume delivery is added to the system's flow control capability when needed. The arrangement is substantially identical to what is illustrated in FIG. 6, but with the addition of a specially designed, variable volume reservoir 102 in which an elastomeric plunger 104 is made to be reciprocally displaceable. More particularly, a stopper 106 having an internally threaded bore seals the top of the reservoir 102 and a threaded shaft 108 having the plunger 104 at one end and a knurled knob 110 at its opposite end is disposed therein. Graduated markings, as at 112, are disposed alongside the threaded knob 110 allowing a predetermined volume to be established below the plunger 104. The outlet port of the reservoir 102 is coupled through a pushbutton actuated relief/one-way valve 114. Pressing the pushbutton opens the valve 114 to allow fluid flow from the driver syringe reservoir into the bolus chamber 102, which serves to reduce the driver syringe volume by the bolus setting volume and consequently delivering the same volume of drug from the drug delivery syringe 20.

A slow-leak flow resistor 116 is arranged to be in fluid communication with the bolus reservoir 102. It functions to allow a slow release of compressed air from the bolus chamber. The depressurizing time is set by sizing this resistance element such that it is ineffective during the short activation time of one-way valve 114. The length of time for depressurizing is calculated as a function of the total desired delivery time and is set to be long enough to discourage overly fast delivery of a drug using repeated bolus use. The flow resistance is smaller, but similar to the flow resistance 52 or 100. It does not require the same level of accuracy as the flow control element for the driver syringe. While a porous frit is shown as being used for the flow resistance element 116 in FIG. 7, a capillary tube, such as used in the embodiment of FIG. 1 may also be used.

Figure 8:
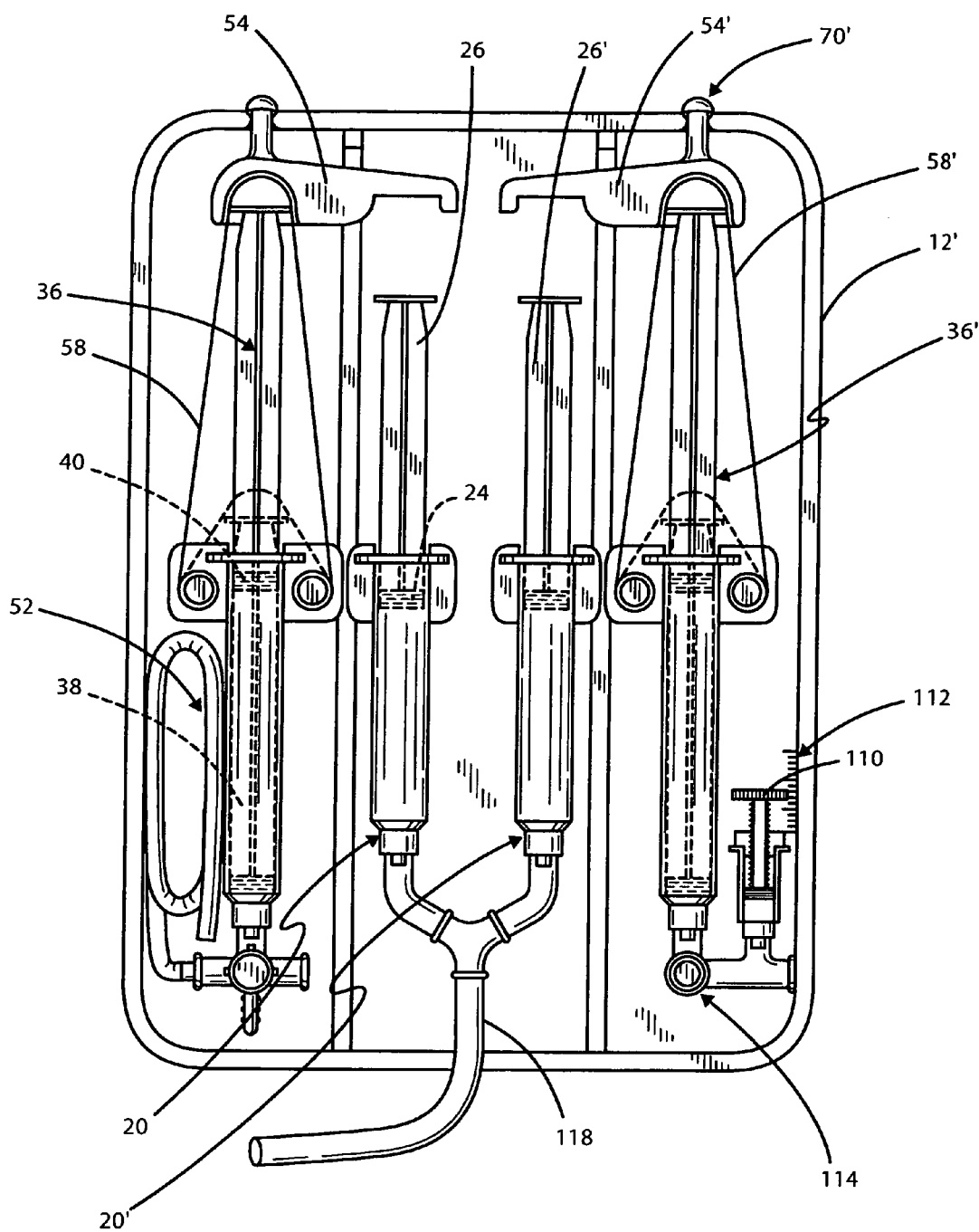
FIG. 8 is an alternative embodiment incorporating a pair of drug delivery syringes and a pair of syringe drivers for simultaneously delivering two drugs, each at its own controlled rate.

Turning next to FIG. 8, an arrangement is shown for delivering both a basal dose and bolus dose through the same drug administration set 118. Here, a three compartment housing 12' contains a basal driver syringe 36, powered by a constant force spring 58 to force a fluid in the driver reservoir 38 from the syringe 36. Flow resistance element 52 effectively controls the rate of descent of the plunger 40 within the reservoir 38. A pusher link 54 is again arranged to engage the plunger shaft 26 and to depress the plunger 24 at a controlled rate, thereby ejecting the medicament as a basal component through the administration set 118. The volume of the bolus dose to be introduced is set by rotating the knurled knob 110 and noting its position along the scale 112. As with the embodiment of FIG. 7, upon depression of the push-button valve 114, fluid flows from the reservoir of the driver syringe 36' such that when the start button 70' is depressed, the constant force spring 58' will cause the pusher linkage 54' to displace the plunger rod 26' thereby rapidly forcing the measured volume of the bolus dose from the drug delivery syringe 20'. Because of the Y-connection of the syringes 20 and 20' with the administration set line 118, both the basal dose and bolus dose can be introduced into the patient simultaneously.

FIGS. 9A-9E illustrate a first embodiment of a multi-mode, rate-control device that is adapted to be coupled to an outlet port of the driver syringe for selectively blocking, producing a "1× flow", a "½× flow", a "2× flow" or a purge of fluid from the administration set. Referring to FIG. 9A, the flow selector is seen to comprise a linear slide valve having a tubular valve housing 120. It has a series of ports 122, 124, 126 and 128 formed through a sidewall thereof. The inside wall of the tubular housing 120 includes an elongated slot 130 spanning a predetermined length of the valve body. Fitted into the valve body 120 is a slidable piston 132 having O-ring seals 134 and 136 disposed in annular grooves in the piston 132. The O-rings 134 and 135 cooperate with the inside wall of the tubular housing 120 to create a seal between the piston and the housing.

A flow resistance element, shown in the form of a capillary tube 138, has one end thereof fitted into the port 122 and its opposite end fitted into the port 124. Similarly, a capillary-type resistance element 140 has a first end disposed in the port 126 and the second end in the port 128. A selector lever 142 has a pointer 144 joined to it. When the pointer is aligned with the legend "stop", fluid from the driver syringe that connects to the inlet 146 of the selector valve is effectively blocked to inhibit movement of the driver syringe's plunger rod.

When the pointer is moved into alignment with the legend "1× flow" as shown in FIG. 9B, fluid from the driver syringe is made to pass through the flow resistance element 138 only. This results in a unit flow rate.

Referring to FIG. 9C, when the pointer 144 is moved into alignment with the legend "½× flow", the fluid from the driver syringe passes through the flow resistance element 138 and the flow resistance element 140 which are effectively connected in series to allow only one-half of the unit flow.

When the pointer 144 is moved to the "2× flow" marker as shown in FIG. 9D, the flow resistance elements 138 and 140 are effectively connected in parallel, allowing double the unit flow rate. More particularly, the fluid exiting the driver syringe reservoir is exposed to both the inlet ports 122 and 126 on the slide valve body. The outlet end of the flow resistance capillary tube 138 at port 124 is exposed through the notch 130 to the atmosphere. Likewise, the outlet end of the capillary flow resistance tube 140 is also exposed to the atmosphere.

When the selector valve 132 is moved to the "purge" position shown in FIG. 9E, fluid entering the inlet end 146 of the slide valve body 120 bypasses the seals on the selector valve 132, via the groove 130, such that no flow resistance element 138 or 140 is in circuit with the fluid being discharged from the driver syringe. This allows the plunger of the driver syringe to descend rapidly and purging air from the administration lines by means of the fluid exiting the driven syringe.

FIGS. 10A-10E describe another embodiment of the rate selector switch. In this arrangement, porous frits as at 150 are used in place of capillary tube flow resistors found in the embodiment of FIGS. 9A-9E. Again, the rate selector comprises a tubular valve body 120' having a slot 130' formed over a predetermined length thereof and with an outlet port 152 that has the flow resistance frit 150 contained therein. A piston or plunger 132' is slidingly received therein, and again, O-ring seals 134 and 136 are disposed within annular slots in the piston. The piston 132' also includes a longitudinal bore 154 containing a flow resistance frit element 156 therein. The bore 154 leads to a radially extending bore 158 that communicates with the gap between the O-ring seals 134 and 136.

Figure 10A:
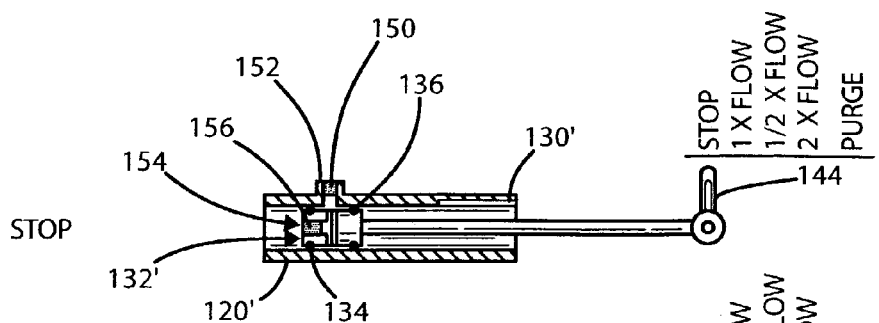
FIGS. 10a through 10e illustrate an alternative embodiment of a rate controller usable with the present invention.
Figure 10B:
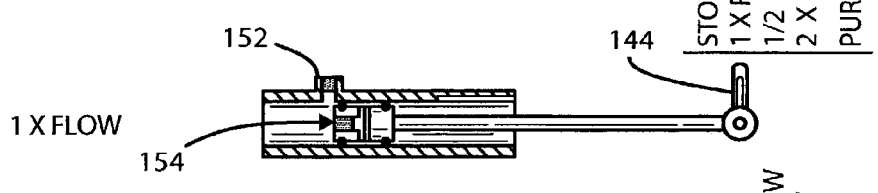
Figure 10C:
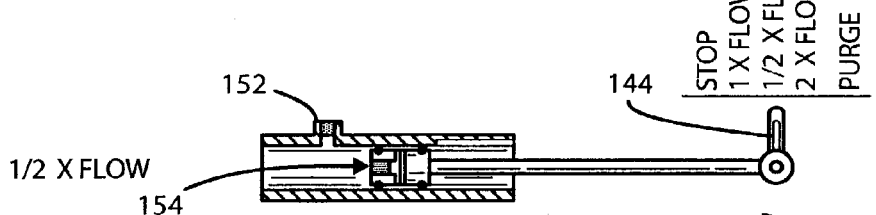
Figure 10D:
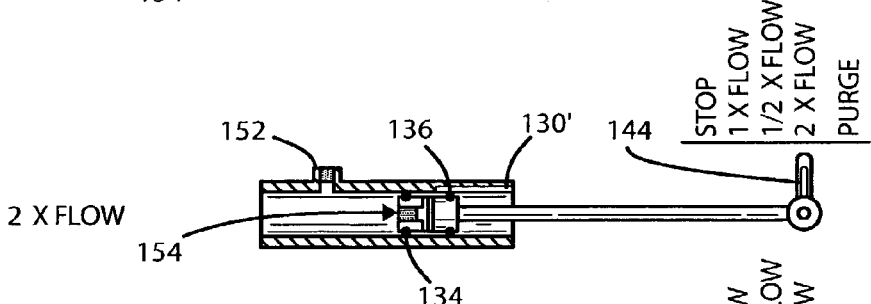

When the pointer 144 is at the "stop" position, as shown in FIG. 10A, fluid from the driver syringe attempting to enter the inlet of the selector valve is totally blocked. Looking next at FIG. 10B, when the selector pointer is aligned with the legend "½× flow", the flow resistance frit elements 156 and 150 are effectively connected in series. When the selector is moved to the position shown in FIG. 10C, fluid can only pass through the resistance element 152. When moved to the "2× flow" position shown in FIG. 10D, fluid from the driver syringe is able to pass through both resistance elements 152 and 156 in that the gap between the O-rings 134 and 136 overlays the notch 130. Thus, flow resistance elements 152 and 156 can be considered to be in a parallel relationship.

Figure 10E:
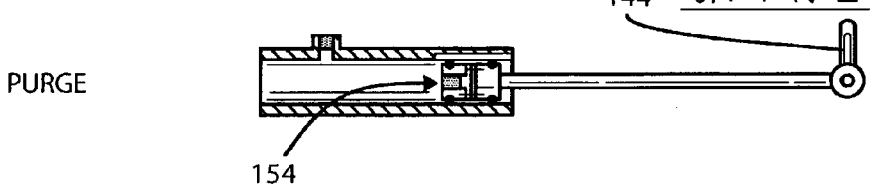

Turning to FIG. 10E, when the selector pointer 144 is moved to the "purge" position, both O-ring seals on the slide valve are bypassed by the notch 130 and the resistance elements 152 and 156 are effectively removed from the outlet of the driver syringe.

Figure 11:
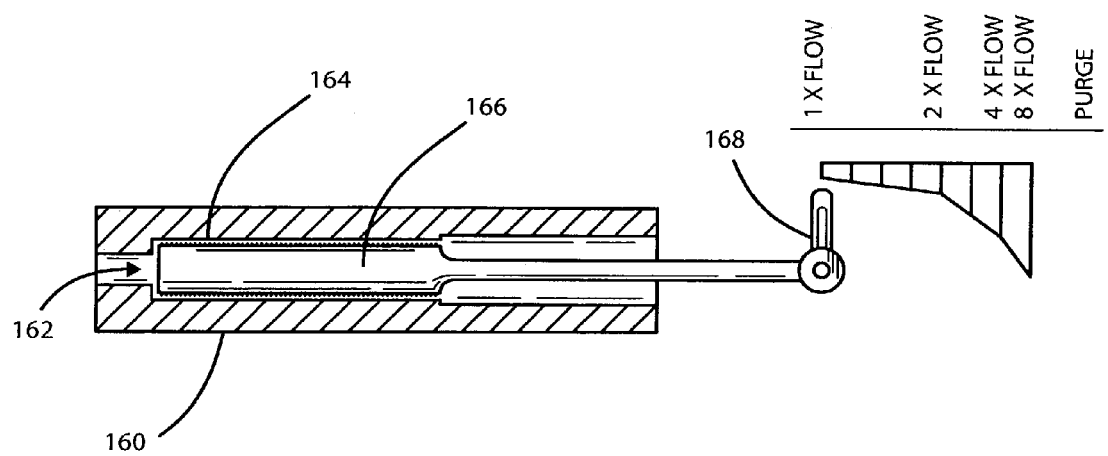
FIG. 11 is yet another embodiment of a flow rate selector usable with the present invention.

FIG. 11 is yet another embodiment of a flow rate selector usable with the present invention. The selector is seen to comprise a tubular body 160 having a longitudinal bore 162 forming a pressure inlet thereof and a counterbore 164 that contains a slidable piston 166 therein. Formed on the surface of the piston 166 is a pattern of microstructure passages similar to a thread on a bolt, but of a much finer depth. The thread cavity can be hollow or possibly filled with a suitable porous substance, such as a fiber bundle. By moving the selector pointer 168 along the scale, the piston 166 moves out of its close fitting sleeve 160 which effectively changes the length of threaded groove through which fluid entering the port 162 must pass. Those skilled in the art will appreciate that the flow resistance of the groove is directly proportional to the engaged length of active groove. Axial motion out of the tight fitting sleeve of the selector housing reduces the length, and consequently, increases the rate of flow of driver fluid.

Figure 12:
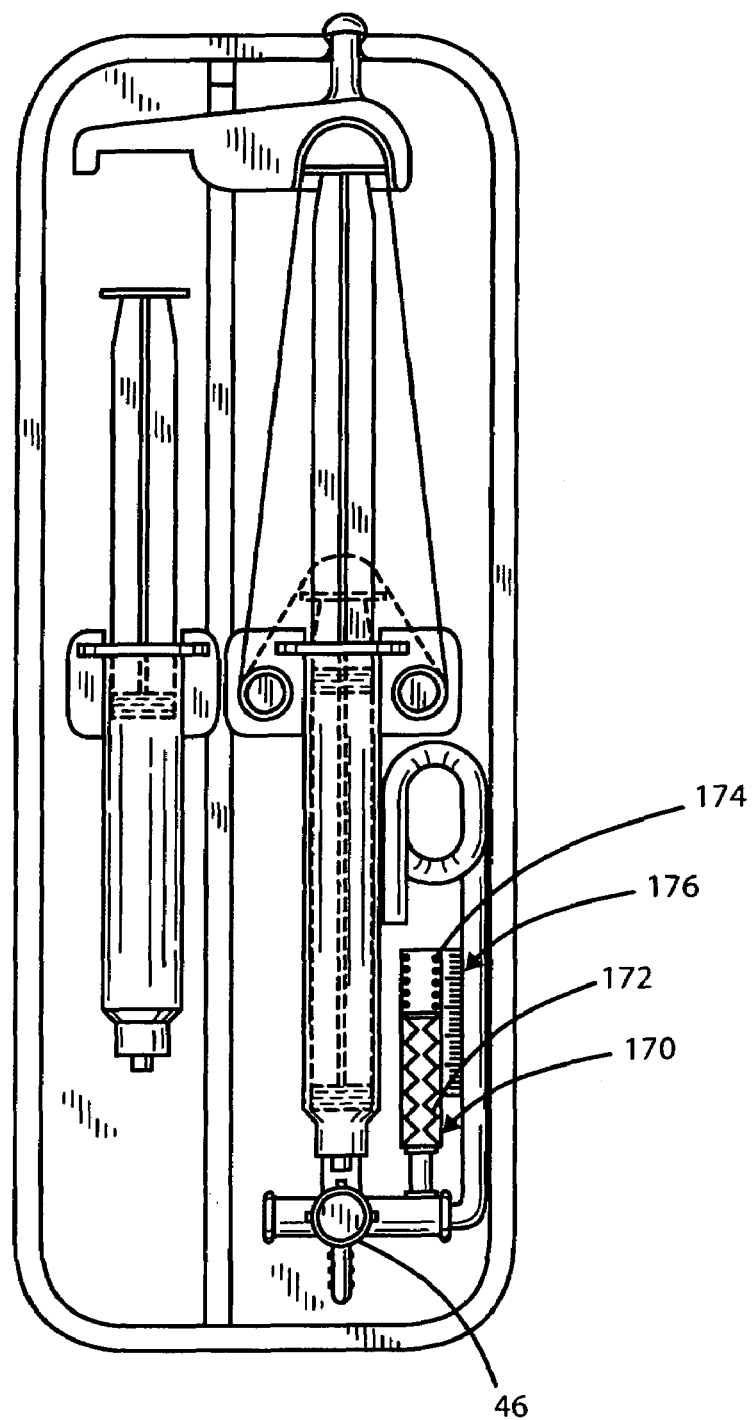
FIG. 12 is a side view of a preferred embodiment incorporating a pressure indicator for the syringe driver.

In may prove expedient to provide a pressure indicator at the outlet of the driver syringe to show normal working pressure as well as drug flow blockage. Referring to FIG. 12, such an indicator may comprise a transparent plastic tube 170 in which is disposed a bellows 172 that works against the force of a coil spring 174 also contained within the tubular chamber 170. The chamber 170 is made to be in fluid communication with the reservoir of the driver syringe when the stop cock 46 is open. The pressure within this closed circuit is then indicated by the position of the top surface of the bellows relative to scale markings on the housing as at 176.

The spring 174 is preferably a linear spring that is used to balance the pressure force, allowing a linear extension of the bellows in response to fluid pressure within the driver syringe reservoir. Those skilled in the art will appreciate that other types of pressure gauges, such as a flexible diaphragm or a bourdon tube may be substituted for the spring-biased bellows arrangement shown in FIG. 12. The scale 176 is preferably configured to show the safe working pressure range and a low pressure warning indicative that the drug delivery administration set may be blocked or kinked.

Figure 13:
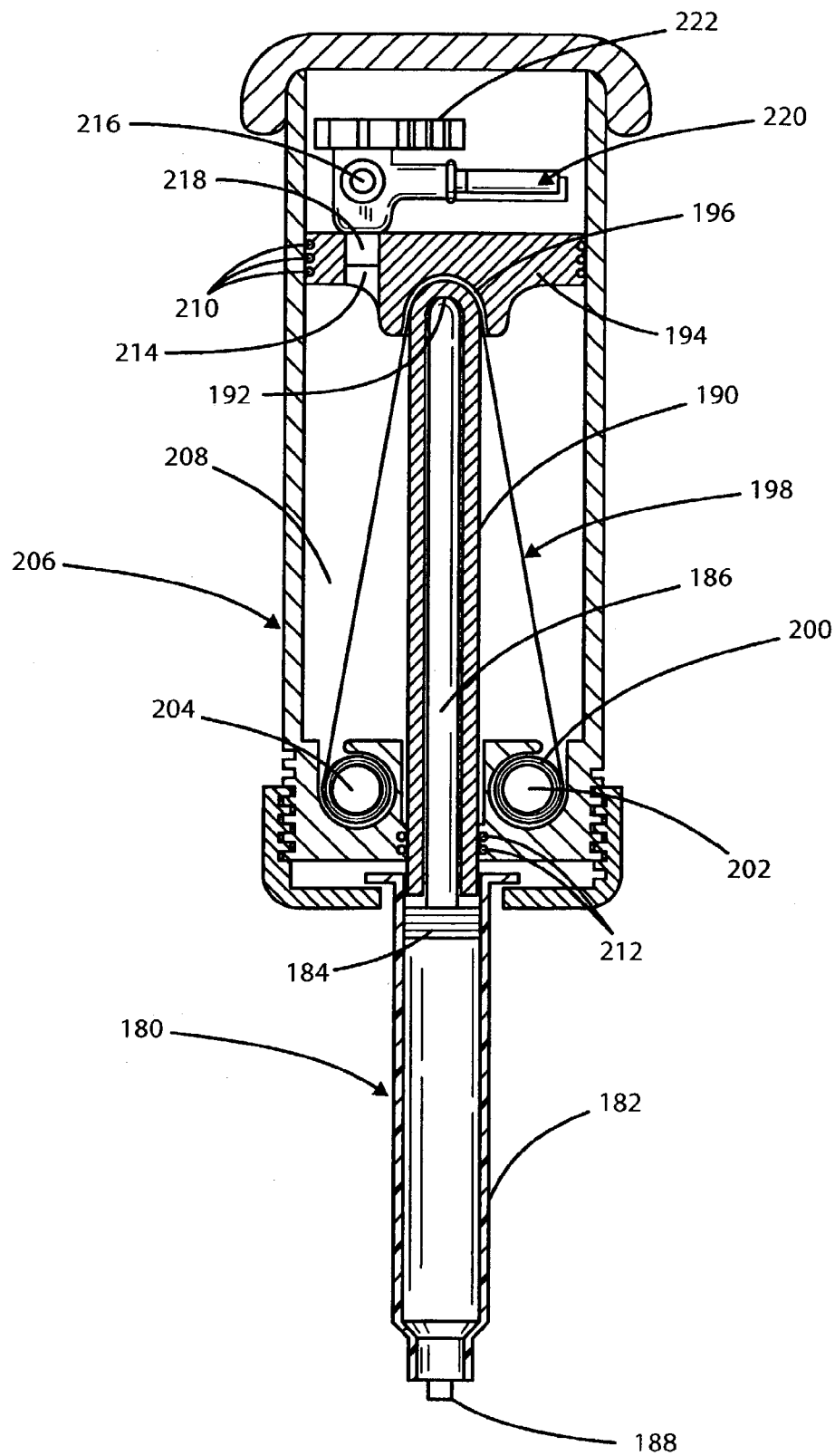
FIG. 13 is a further alternative embodiment showing a further possible placement of the driver syringe relative to the drug delivery syringe.

In each of the previously described drug delivery systems, the driver syringe and the drug delivery syringe are placed in a generally side-by-side relationship within an outer container or housing. FIG. 13 shows an embodiment in which the drive syringe and the drug delivery syringe are oriented generally coaxially. In the arrangement of FIG. 13, the drug delivery syringe is identified by reference numeral 180 and it comprises a reservoir 182 that is generally circular in cross-section and disposed within it is an elastomeric plunger member 184 which is disposed on the proximal end of a plunger rod 186. As the plunger 184 is made to descend, it forces the medicament from the reservoir 182, via the syringe outlet port 188.

Fitted over the plunger rod 186 is a tube 190 having a closed rounded upper end 192 to which a further piston 194 is affixed. The piston 194 has an arcuate slot 196 for accommodating a segment of a constant force spring 198. The constant force spring has a pair of reels as at 200 surrounding centerposts 202 and 204. Surrounding the piston 194, and the pusher assembly 186 and 190 is an outer cylinder 206 that is adapted to contain either a compressible or an incompressible fluid in a reservoir 208 in which the piston 194 may slide. O-ring seals as at 210 prevent the escape of the fluid, via the interface between the piston 194 and the walls defining the reservoir 208. Likewise, O-ring seals 212 are provided to block flow of the fluid contained in the reservoir 208 along the surface of the tubular pusher 190.

A bore 214 is formed through the thickness dimension of the piston 194 and a stop cock 216 having an inlet 218 is fitted into this bore. The outlet of the stop cock 216 connects to a flow resistance device 220 which, as in the earlier embodiments, may comprise a capillary tube of a predetermined length and inside diameter or a calibrated porous frit.

With the stop cock lever 222 in a position to block fluid flow, the piston 194 remains stationary. However, when the stop cock lever 222 is moved to open this valve, the pressure within the reservoir 208 caused by the force of the spring 198 results in the fluid escaping from the reservoir 208 through the stop cock and the rate control element 220, allowing the piston 194 to descend at its controlled rate. As the piston 194 descends, it displaces the plunger 184 of the drug delivery syringe 180, ejecting a medicament out the port 188.

Figure 14:
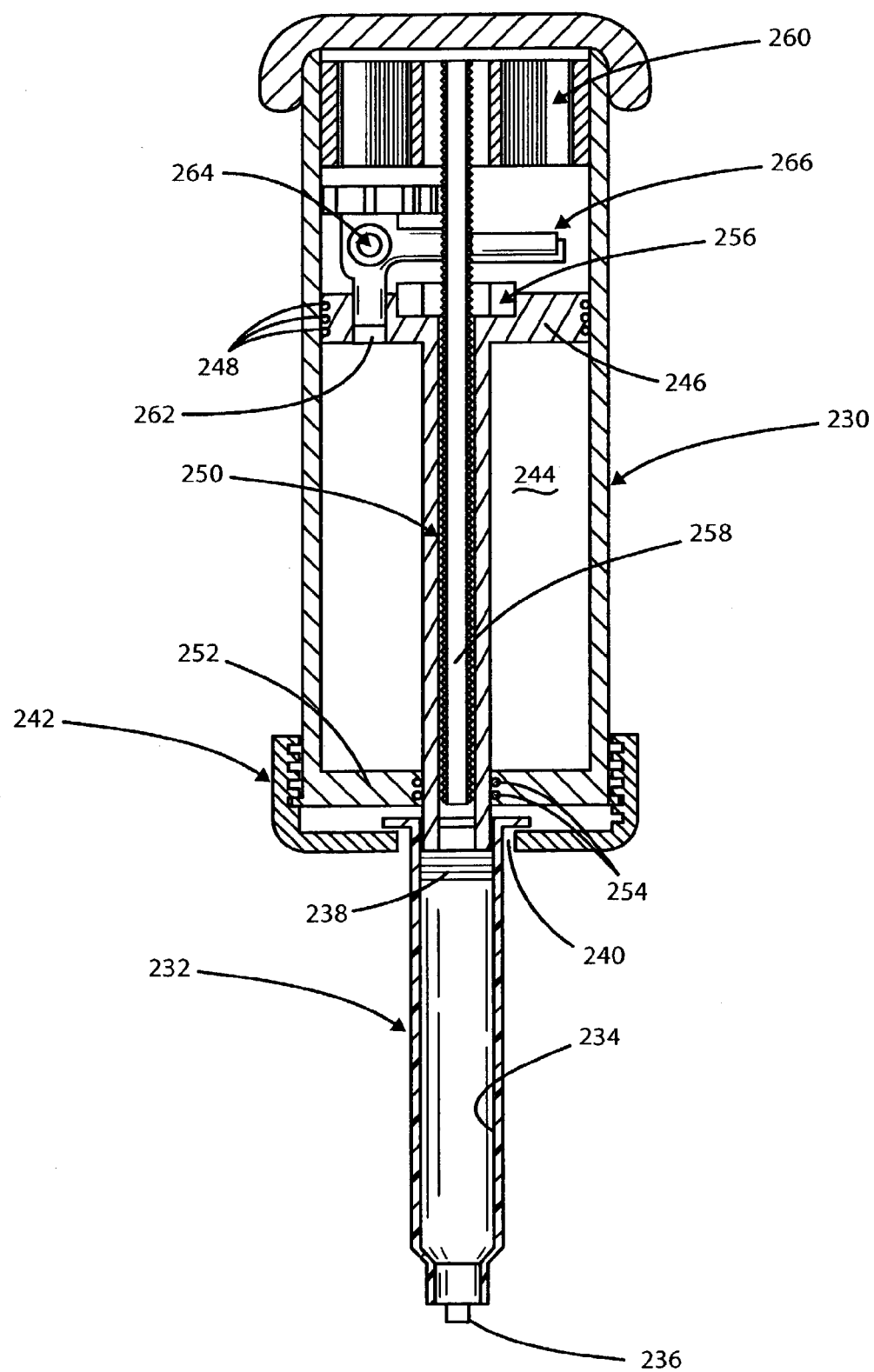
FIG. 14 is a further preferred embodiment using a rotary constant force spring in the driver syringe.

FIG. 14 shows still another embodiment of the present invention. Here, rather than having a linear constant force spring to provide the driving force, a constant torque helically wound spring is employed. As in the embodiment of FIG. 13, the driving syringe and the drug delivery syringe are generally coaxially disposed. The driving syringe is generally identified by numeral 230 while the drug delivery syringe is identified by numeral 232. The drug delivery syringe 232 includes a reservoir 234 having an outlet port 236 for delivery of a medicament therethrough. Disposed in the reservoir 234 is a complimentary fitting piston 238, preferably formed from an elastomeric material so as to provide a fluid tight seal with respect to the inner wall of the reservoir 234. The drug delivery syringe 232 is adapted to fit through an opening 240 formed in the base of a cap 242 that can be screwed or otherwise clamped to the lower end of the drive syringe 230.

The drive syringe itself includes a reservoir 244 that is adapted to contain either a compressible or an incompressible fluid therein. The reservoir 244 may be of a circular or an oval cross section and disposed in it is a complimentary shaped piston 246. O-ring seals 248 are operatively disposed between the periphery of the piston 246 and the inner wall of the reservoir 244. The piston 246 is disposed proximate a first end of a tubular pusher 250 that is adapted to cooperate with the plunger 238 of the drug delivery syringe 232. The tubular pusher 250 passes through a bore formed in a bottom or base 252 of the reservoir 244 and O-ring seals 254 are used to prevent leakage of fluid past that interface.

A traveling nut 256 is fitted into a recess formed in the upper surface of the piston 246 and a threaded rod 258 passes through the internally threaded bore of the nut 256. Secured in driving relation to the threaded rod 258 is a constant torque, helically wound spring 260.

With continued reference to FIG. 14, it can also be seen that a bore 262 is formed through the thickness dimension of the piston 246 and fitted into this bore is the inlet port of a stop cock 264. The outlet port of the stop cock is fitted with a rate controlling member 266, here again shown as a predetermined length of capillary tubing. With the stop cock is closed, the piston 246 is at rest at an equilibrium point between the driving force produced by the spring 260 on the piston 246 by way of the threaded pusher 258 and traveling nut 256 and the force produced by the pressurized fluid within the reservoir 244 acting on the surface area of the piston 246. Now, when the stop cock is opened, the fluid may flow through the bore 262 and the stop cock and through the flow restriction offered by the capillary tube 256 thereby allowing the piston 246 to be driven downward as the shaft 258 is made to rotate. The downward movement of the piston 246 drives the plunger 238 of the drug dispensing syringe 232, via the tubular pusher 250. The rate at which the plunger 238 moves is, of course, a function of the flow resistance element 266.

Figure 15A:
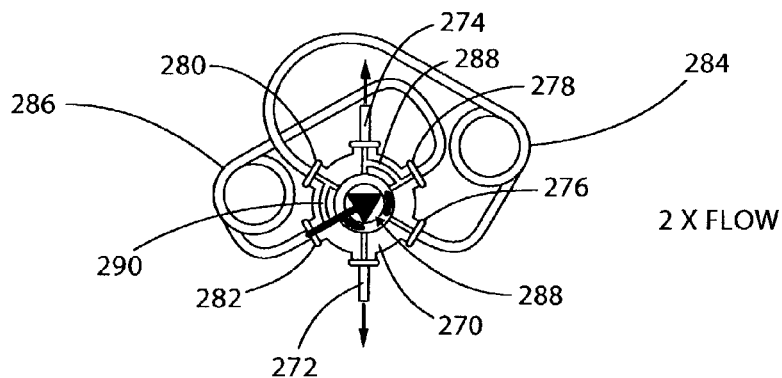
FIG. 15 is a flow selector device suitable for the embodiment of FIG. 13 and FIG. 14.

FIGS. 15A-15D illustrate the design of a rotary flow rate control for use with the driver syringe of the earlier described embodiments. It is seen to comprise a manifold 270 having an inlet port 272 that is adapted to be connected to the outlet port of the driver syringe. The manifold 270 also has an outlet port 274 opened to the atmosphere. In addition to the inlet port 272 and the outlet port 274, the manifold 270 also includes a series of radial ports 276-282. A first flow resistance capillary tube 284 connects between the radial port 276 and 280. A second flow resistance element 286 is coupled between the radial ports 278 and 282. A rotary member, indicated by the arrow 288, cooperates with the manifold 270 to selectively connect the radial ports to one another in a predetermined fashion whereby 2× Flow, ½ × Flow, 1× Flow and a stop condition can be realized. When the rotary member 288 is positioned as illustrated in FIG. 15A, fluid entering the inlet port 272 is made to flow through the resistor element 286 to the manifold port 278 and from there through a connecting branch 288 to the outlet port 274. At the same time, the fluid entering the inlet port 272 flows through the manifold passage 290 and the radial port 280 through the resistance element 284 and thence back through the branch 288 to the outlet port. Thus, the flow resistance elements 284 and 286 are effectively connected in parallel whereby double the unit flow occurs.

Figure 15B:
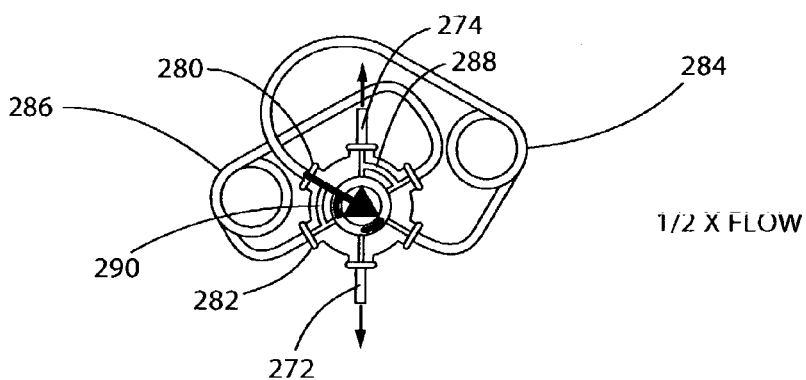

In FIG. 15B, the fluid entering the inlet port 272 is made to flow through the resistance element 284, to the radial port 280, and from there, through the passage 290 and the radial port 282, through the flow resistance element 286 and the channel 288 to the outlet port 274. Thus, the resistance elements 284 and 286 are effectively connected in series cutting the unit flow rate in half.

Figure 15C:
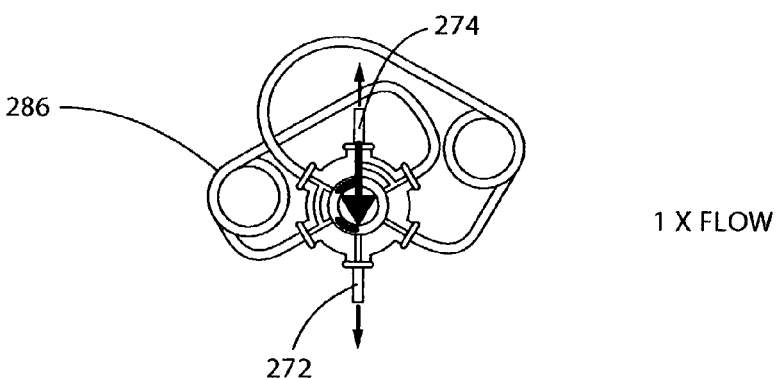

When the rotary selector is set as shown in FIG. 15C, the only path between the inlet port 272 and the outlet 274 is via resistance element 286 resulting in a unit flow rate.

Figure 15D:
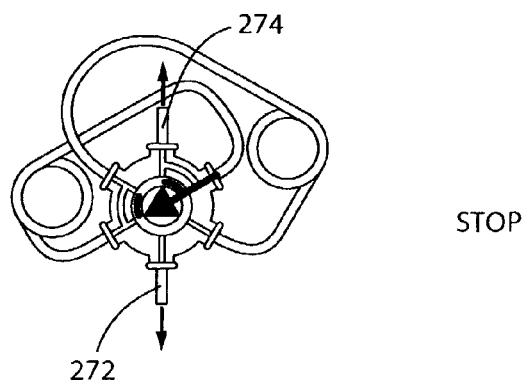
Figure 16A:
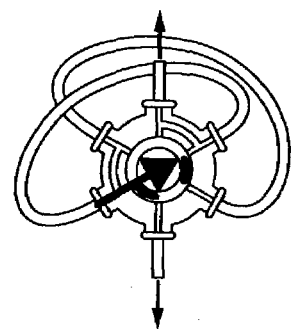
FIG. 16 is an alternative flow selector suitable for the embodiment of FIG. 13 and FIG. 14.
Figure 16B:
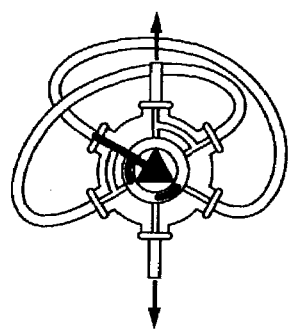
Figure 16C:
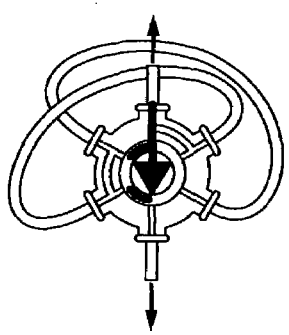
Figure 16D:
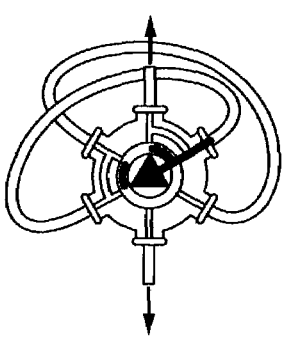

When the rotary selector is positioned as shown in FIG. 15D, there is no flow path from the inlet port 272 to the outlet port 274, a no-flow or "stop" condition.

FIGS. 16A-16D shown another embodiment of a rotary flow selector device that utilizes porous frits as the flow resistance element rather than capillary tubes. From what has been heretofore explained with respect to FIG. 15, it is believed that readers reasonably skilled in the art will be able to trace through the flow paths to confirm that the disclosed mechanism of FIGS. 16A-16D can selectively provide two times unit flow rate, one-half unit flow rate, unit flow and a stopped or blocked condition. Hence, it is not deemed necessary to set forth the analysis in detail.

As with any of the foregoing embodiments, the selection of the driver fluid, i.e., that contained within the reservoir of the driver syringe, depends on desired delivery flow rate and the cost of manufacturing. For any possible flow rate requirement, a compressible driver fluid, such as air, is preferred. For applications, such as hyperbaric infusion, an inert gas, such as nitrogen or carbon dioxide, is offered in a pre-filled driver syringe or a pressurized canister to fill the driver syringe that has an appropriate filling connector. For very slow infusion application, an incompressible fluid, such as saline, an oil of a desired viscosity, or highly wettable and stable solutions may be used for the driving fluid in the driver syringe. For such liquid application of driver fluid, an inflatable bag is provided as a container for the metered driver fluid exiting the flow resistance element.

It can be seen, then, that the present invention provides the mechanical equivalent of an electronic syringe pump that is capable of providing a controlled motion pattern to the plunger of a drug delivery syringe. Because of the unique design described in which a driver syringe, that is powered by a constant force or constant torque spring (depending on the embodiment under consideration), to effect displacement of the plunger of the drug delivery syringe or vial, flow resistance elements which might be incompatible with the drug involved need not be disposed in the drug flow path leading to the patient, but instead, may be used with the driver syringe that is totally isolated from the drug delivery syringe. This leads to a further advantage in that the drug delivery rate is independent of the concentration and viscosity of the drug.

This invention has been described herein in considerable detail in order to comply with the patent statutes and to provide those skilled in the art with the information needed to apply the novel principles and to construct and use such specialized components as are required. However, it is to be understood that the invention can be carried out by specifically different equipment and devices, and that various modifications, both as to the equipment and operating procedures, can be accomplished without departing from the scope of the invention itself.

What is claimed is:

1. A fluid dispensing device comprising:
    (a) a first syringe having a reservoir with an outlet port, the reservoir adapted to hold a liquid medicament to be dispensed, and a plunger for ejecting the liquid medicament from the reservoir through the said outlet port;
    (b) a second syringe having a reservoir with an outlet port, the reservoir of the second syringe adapted to contain a fluid, and a plunger for ejecting the fluid from the second reservoir;
    (c) a link member coupling the plunger of the second syringe to the plunger of the first syringe so that both said plungers will move in unison;
    (d) a double coil constant force spring or a helically wound constant torque spring contiguously coupled to the plunger of the second syringe to impart a generally constant force to the plunger of the second syringe; and
    (e) a flow rate control device coupled only to the outlet port of the reservoir of the second syringe for controlling the rate of displacement of the plunger of the first syringe as it is made to move in unison with the plunger of the second syringe.

2. The fluid dispensing device as in claim 1 wherein the flow rate control device comprises a length of tubing of a predetermined fluid resistance.

3. The fluid dispensing device as in claim 2 and further including a collection chamber coupled to the tubing for receiving fluid exiting the tubing.

4. The fluid dispensing device as in claim 2 and wherein the length of tubing is coupled to the outlet port of the reservoir of the second syringe by a stop cock.

5. The fluid dispensing device as in claim 1 and further including a housing member for retaining the first and second syringes in a side-by-side orientation.

6. The fluid dispensing device as in claim 1 wherein the outlet of the reservoir of the first syringe is connected to a device for infusing a fluid into a patient's body.

7. The fluid dispensing device as in claim 1 wherein the fluid in the reservoir of the second syringe is a gas.

8. The fluid dispensing device as in claim 1 wherein the fluid in the reservoir of the second syringe is a liquid.

* * * * *